United States Patent [19]
Edeling et al.

[11] Patent Number: 4,609,972
[45] Date of Patent: Sep. 2, 1986

[54] METHOD FOR THE MANUFACTURE OF POROUS VITREOUS CARBON

[75] Inventors: Martin Edeling, Essen; Ulrich Gebhardt, Langensendelbach, both of Fed. Rep. of Germany

[73] Assignee: Siemens Aktiengesellschaft, Munich, Fed. Rep. of Germany

[21] Appl. No.: 763,534

[22] Filed: Aug. 7, 1985

[30] Foreign Application Priority Data

Aug. 13, 1984 [DE] Fed. Rep. of Germany ....... 3429794

[51] Int. Cl.[4] .................... H01G 9/00; C01B 31/00
[52] U.S. Cl. ................................. 361/433; 423/448
[58] Field of Search ............... 423/448; 361/433 A, 361/433 S

[56] References Cited

U.S. PATENT DOCUMENTS

| 3,446,593 | 5/1969 | Moutaud | 423/448 |
| 3,652,902 | 3/1972 | Hart et al. | 361/433 |
| 4,327,400 | 4/1982 | Muranaka et al. | 361/433 |
| 4,394,713 | 7/1983 | Yoshida | 361/433 |

FOREIGN PATENT DOCUMENTS

42581 3/1982 Japan .................. 423/448

Primary Examiner—Donald A. Griffin
Attorney, Agent, or Firm—Kenyon & Kenyon

[57] ABSTRACT

Porous vitreous carbon with good electrical and mechanical properties as well as large double-layer capacitance can be produced by hardening and pyrolysis of thermosetting carbonizable resins including about 1 to 10 weight-percent of a salt of a fatty acid having about 10 to 20 carbon atoms which is soluble in the resin and can be volatilized without residue.

15 Claims, 1 Drawing Figure

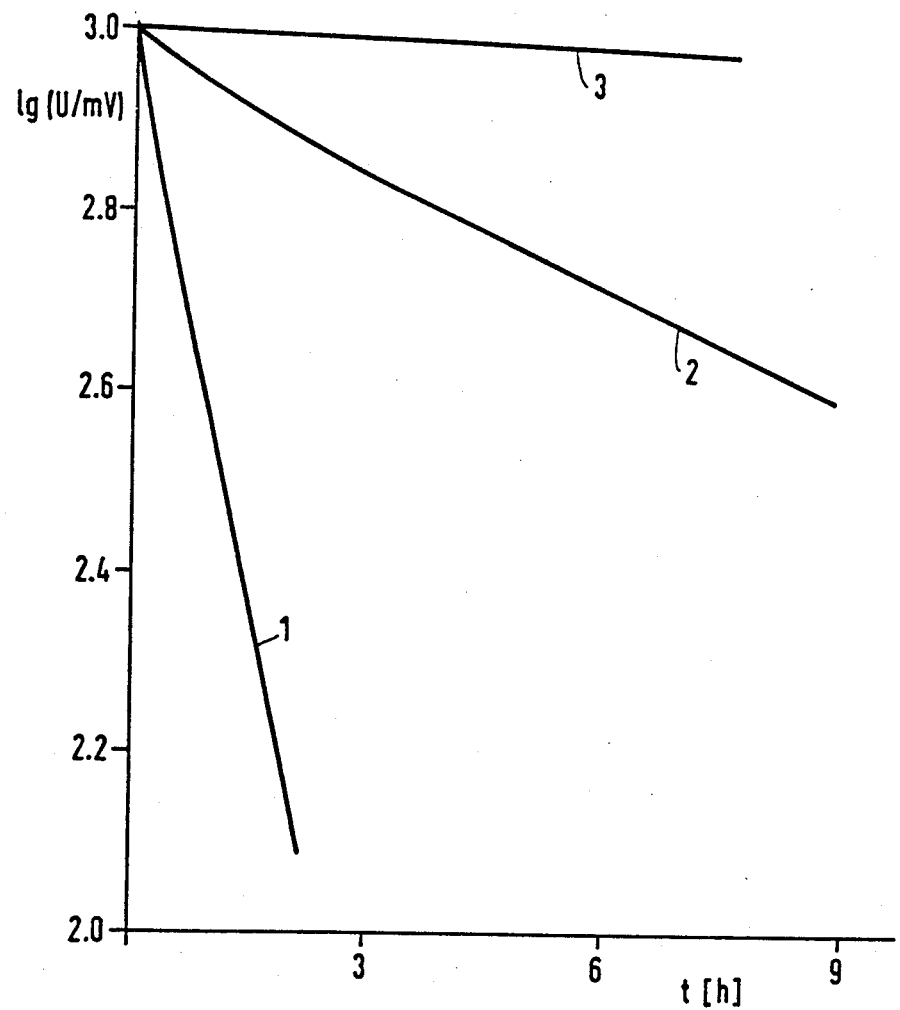

METHOD FOR THE MANUFACTURE OF POROUS VITREOUS CARBON

FIELD OF THE INVENTION

The present invention relates to a method for the manufacture of porous vitreous carbon by hardening and pyrolysis of thermosetting carbonizable resins. The porous vitreous carbon may be used as electrode material for electrochemical double-layer capacitors and the like.

BACKGROUND OF THE INVENTION

Capacitors having a large capacitance per unit volume can be made by utilizing an electrochemical double layer. Such electrochemical double-layer capacitors comprise a plurality of porous electrodes having a large internal surface area, the electrodes being in contact with an electrolyte having high conductivity. In multi-cell designs in order to realize nominal voltages higher than the decomposition voltage of the electrolyte, the individual electrolyte chambers must be separated from each other.

The large internal surface area required for such electrodes can be achieved, for instance, by using bound activated carbon (DE-OS 30 00 777 or U.S. Pat. No. 4,327,400 and DE-OS 30 46 252 or U.S. Pat. No. 4,394,713) or activated vitreous carbon (DE-OS 30 11 701 or "Chemical Abstracts", vol. 95 (1981) no. 22 (page 640), 196226g). In this connection, activated vitreous carbon provides good electrical and mechanical properties, it is easily shaped and provides the required gas-tightness. However, only relatively thin layers of activated vitreous carbon with a thickness of about 10 to 50 $\mu$m can be produced by conventional methods and consequently they only produce a capacitance of some 100 mF·cm$^{-2}$. On the other hand, a double layer capacitance of up to 10 F·cm$^{-2}$ can be achieved with bound activated carbon due to its high porosity (with electrodes about 1 mm thick). However, these electrodes must be supported mechanically and individually sealed. Furthermore, only moderate electronic conductivities may be realized in these capacitors because of the binders used.

SUMMARY OF THE INVENTION

It is an object of the present invention to develop a method for the manufacture of vitreous carbon from thermosetting carbonizable resins in such a manner that the vitreous carbon has good electrical and mechanical properties, and is capable of producing a large double-layer capacitance.

According to the invention this is achieved by adding to a carbonizable thermosetting resin about 1 to 10 weight percent of a salt of a fatty acid having about 10 to about 20 carbon atoms and which is soluble in the resin and can be volatilized without leaving a residue.

The present invention provides a method for manufacturing vitreous carbon by hardening and pyrolysis of a thermosetting carbonizable resin, characterized by the feature that said resin includes about 1 to 10 weight percent, referred to the weight of the resin, of a fatty acid salt having about 10 to 20 carbon atoms which is soluble in said resin and can be volatilized without leaving a residue. Volatilized without residue means that enough of the fatty acid salt is eliminated from the resin to form the desired pore structure and any remaining fatty acid salt or pyrolysis products thereof will be insufficient to have a significant adverse affect on the electrical properties of the vitreous carbon so formed.

The vitreous carbon produced by the method according to the invention combines the good electrical and mechanical properties of vitreous carbon with the large double-layer capacitance capability of activated carbon due to its high porosity. The reason for this porosity is that the fatty acid salt added to the resin functions as a pore former which produces macroporosity. The macropores formed in the vitreous carbon due to addition of the pore former to the resin typically have a diameter in the $\mu$m range (10$^{-6}$ m).

BRIEF DESCRIPTION OF THE DRAWING

FIG. 1 is a charge/discharge curve for a capacitor constructed in accordance with the invention.

DETAILED DESCRIPTION OF THE INVENTION

Due to its good properties, the porous vitreous carbon produced by the method according to the invention is highly suited for the electrode material in electrochemical double-layer capacitors. Electrodes of such a material are not only mechanically stable and gas-tight, but also have a high electrical conductivity and a large double-layer capacitance. Capacitors with such electrodes are therefore especially well suited for use in an emergency power supply for integrated semi-conductor memories used in the event of network interruptions.

The manufacture of macroporous vitreous carbon is already known per se (British Pat. No. 1,031,126 and U.S. Pat. No. 3,446,593). In the reference processes a highly porous vitreous carbon is produced using a macroporous support material such as polyurethane foam impregnated with a thermosetting resin and the impregnated support material is subsequently carbonized. However, the product of such processes is not suited for producing electrodes with a high double-layer capacitance because it is too porous for this purpose having a sponge-like structure. In addition, the "macropores" are generally so large (larger than about 0.1 mm) that the material is highly gas and liquid-permeable.

In the method according to the invention, furfuryl alcohol or a phenol-furane resin is preferably used as the carbonizable resin. Other useful thermosetting carbonizable resins well known in the art, can also be used, for example, phenolformaldehyde resins.

According to the invention, a salt of a fatty acid or several of such salts are mixed with a thermosetting carbonizable resin prior to hardening and pyrolysis of the mixture.

The term "fatty acids" as used herein includes aliphatic carboxylic acids of the general formula RCOOH, wherein R is a saturated or unsaturated organic group having about 10 to 20 carbon atoms.

In the method according to the invention, derivatives of fatty acids having 10 to 20 carbon atoms are used, i.e., derivatives of so-called medium or higher fatty acids. The fatty-acid derivatives are added to the resin, in amounts of about 1 to 10 weight percent and preferably 4 to 5 weight percent based on the weight of the resin. The fatty-acid derivatives are salts, i.e., compounds of the general formula RCOOM (M=metal) preferably zinc stearate ($C_{17}H_{35}COOZn$) or zinc undecylenate ($C_{10}H_{19}COOZn$). Stearic acid is a saturated fatty acid; undecylenic acid (or 10-undecene acid) is a single unsaturated fatty acid. Other salts that can be used are, for instance, magnesium stearate and salts of palmitic acid ($C_{15}H_{31}COOH$). The salts used must be soluble in the carbonizable resin which means that they are soluble either in resin starting materials, e.g., monomer, or become solublized during polymerization of the resin.

The carbonizable resins or plastics may be hardened with basic or acid compounds. In the method according to the invention, strong acids are generally used as hardeners and p-toluenesulfonic acid is a preferred hardner. The hardening process preferably takes place at temperatures of about 150° to 200° C. and is completed in about 1 to 5 hours.

A procedure for the manufacture of electrodes is generally as follows. A thermosetting carbonizable resin including a pore forming fatty acid salt is first polymerized at temperatures of up to about 100° C. From this resin polymerisate, which is advantageously in the form of a flexible foil, electrode blanks of the desired shape are then produced, e.g., by stamping or like cutting methods. The linear shrinkage of the polymerisate typically about 20% during the pyrolysis step must be taken into account here. The resulting electrode blanks are then hardened. After the hardening, the blanks may be further machined (shaped) mechanically, if required. The shaped electrode blanks are then subjected to the pyrolysis.

The pyrolysis is preferably carried out at temperatures of up to about 1100° C. By pyrolysis the thermosetting plastic is carbonized and thereby converted into vitreous carbon. At the same time, the pore former, i.e., the salt of a fatty acid, is sublimated or volatilized, whereby a macroporous structure is formed in the vitreous carbon. The volatilization is substantially complete that is after pyrolysis almost all of the fatty acid is eliminated from the vitreous carbon. The duration of the pyrolysis may be about 12 to 36 hours (including heating-up and cooling-down time), and is preferably about 24 hours and the final pyrolysis temperature is maintained for about 1 to 5 hours.

The vitreous carbon obtained by the pyrolysis may advantageously be converted to activated vitreous carbon, especially if it is to be used as an electrode material. In this process, a microporous structure with pores in the nm range ($10^{-9}$ m and below) is superficially generated on the vitreous carbon. By the activation, which is preferably carried out by annealing in air at temperatures between 450° and 500° C. (duration: about 3 to 5 hours) the double-layer capacitance of the vitreous carbon, e.g., electrodes, can be further increased.

Vitreous carbon produced and activated by the method according to the invention has, for instance at a layer thickness of about 1 mm, a double-layer capacitance of more than about 10 $F \cdot cm^{-2}$ (with 3.6M $H_2SO_4$ electrolyte). As in the case of activated carbon, the capacitance is a frequency-dependent property, where the full capacity is usually obtainable at frequencies below 1 to 10 mHz. The electrical resistivity of the porous vitreous carbon is typically less than 10 mohm·cm.

Besides use as electrode material for electrochemical double layer capacitors, the vitreous carbon produced by the method according to the invention has other advantageous uses for example, the manufacture of electrodes which find the use in electromedicine. These are primarily stimulation electrodes, especially for heart pacemakers (see in this connection DE-OS 26 13 072).

The invention will be explained in still further detail by making reference to the following examples and FIG. 1.

EXAMPLE I

A procedure for manufacturing macroporous vitreous carbon electrodes having large double-layer capacitance is, for instance, as follows: about 150 ml furfuryl alcohol and 7.5 g zinc stearate (about 4.4 weight-percent) are mixed by stirring. Subsequently, 15 ml of a 10 percent solution of p-toluenesulfonic acid in ethanol (hardener solution) is added. The mixture is further stirred at room temperature for about 2 hours; then poured on a sheet (30 cm×30 cm) of polypropylene heated to 80° C. and kept at this temperature over night to form a flexible self-supporting foil having a thickness of about 1.5 mm. Electrode blanks with the desired dimensions are punched out of the foil. These blanks are then hardened at a temperature of about 200° C. for about 1 hour.

To ensure high gas-tightness the electrodes may, additionally, be sealed. If this is to be done on only one side, the procedure is as follows: the blanks are sandblasted and coated on one side with resin (20 ml furfuryl alcohol+1 ml of the above-mentioned hardener solution) and hardened under an IR radiator. This coating procedure may be repeated if desired. Electrodes treated in this manner exhibit a helium leakage rate of only $10^{-7}$ mbar·l·s$^{-1}$·cm$^{-2}$. It is also possible to cement two electrodes together in order to produce symmetrical gas-tight electrodes for a bipolar arrangement using the above-described procedure.

The hardened electrode blanks are then subjected to pyrolysis. To this end, they are heated in an inert gas atmosphere, for instance, in argon, to a temperature of 1100° C. for about 24 hours. During pyrolysis, the zinc stearate pore former is volatilized out of the blank producing a macroporous structure in the vitreous carbon formed by carbonization of the resin. The macroporous structure can be seen clearly in a scanning electron microscope.

Finished electrodes having an electrode surface of 4.9 $cm^2$ and a thickness of 1 mm were examined for zinc residues by means of an electron beam X-ray microanalysis. No zinc could be detected either on the surface or in the pores, with a detection limit of below 0.1 weight-percent. The electrical resistivity of such vitreous carbon electrodes was found to be 4.5 mohm·cm; which is negligible compared to the electrolyte resistivity in a double layer capacitor. The electrical resistance may depend on the final pyrolysis temperature employed.

The electrodes may be activated by annealing at about 470° C. for about 3 hours in air. Capacitance measurements on such electrodes are made in a half cell with 3.6 m $H_2SO_4$ as the electrolyte. The double-layer capacitance can be determined here by applying a triangle voltage as well as by impedance measurements. It is to be taken into account that full capacitance is available only at small voltage application rates or low frequencies. In potentiondynamic measurements between 100 and 300 mV vs. $H_2$rev and at a feeding rate of $10^{-4}$ V/s, capacities of 12.5 F·cm$^{-2}$ are obtained (electrode thickness: 1 mm). It is found from impedance measurements that the capacitance drops above 10 mHz due to the pore structure. At 1 mHz, the capacitance is about 10.9 F·cm$^{-2}$; which corresponds to a volume capacitance of about 100 F·cm$^{-3}$.

Using two vitreous carbon electrodes prepared in the manner described above, a single-cell capacitor is constructed using 3.6 m $H_2 SO_4$ as electrolyte. For making electrical contact a copper plate is cemented to each electrode back-side and a feed cable is soldered thereto. On such a capacitor, a capacitance of 30 F is measured, which corresponds to an area capacitance of 12.2 F·cm$^{-2}$.

With the described capacitor, charging and discharging curves were recorded. If the completely discharged capacitor is charged to 1 V, a residual current of 1.8 mA still flows after one hour (with an electrode surface of 4.9 cm$^2$); after 16 hours a current of 0.1 mA still flows.

In FIG. 1, charge/discharge curves are shown specifically with a load resitance R of 100 ohms (curve 1), 1 kohm (curve 2) and $10^4$ kohm (curve 3) i.e., for self-discharge. The nearly straight shape of the curves indicates an ideal capacitor. From the self-discharge, a leakage resistance of 15 kohm is calculated and therefrom a capacitance of 37 F is derived, which corresponds to an area capacitance of about 15 F·cm$^{-2}$.

EXAMPLE II

Additional macroporous vitreous carbon electrodes may be prepared in the following manner:

(a) 150 ml furfuryl alcohol is reacted with 7.5 g zinc undecylenate and 10 ml of a 20 percent solution of p-toluenesulfonic acid in ethanol and stirred at room temperature for 2 hours. The mixture is then poured out onto a substrate of polypropylene and polymerized over night at a temperature of 90° C. forming a flexible self-supporting foil which is processed further, in the manner described above, to form electrodes. The electrodes obtained after the pyrolysis and subsequent activation (5 hours at 470° C. in air) have a double-layer capacitance of 2 F·cm$^{-2}$ and 25 F·cm$^{-3}$, and a thickness of 0.8 mm.

(b) 20 g of a commercially available phenol-furane resin is reacted at 50° C. with 1 g zinc stearate and then stirred intensively. Subsequently, 1 ml of 20 percent solution of p-toluenesulfonic acid in ethanol is added and the mixture is polymerized at 80° C. in the manner described above. After hardening, pyrolysis and activation (5 hours at 470° C.) electrodes are obtained which have a double-layer capacitance of 3 F·cm$^{-2}$ for a thickness of 1 mm.

The method of the present invention is not limited to the embodiments described in the above examples; rather it can be varied in many respects as will be appreciated by those skilled in the art, for example, the resin can be polymerized in two steps. The two-step procedure involves initially adding only part of the total hardener required to the resin, i.e., a first step. The resulting resin prepolymerisate can then be stored at room temperature for some time, e.g., up to several days, and then polymerized completely in a second step with the addition of the remaining hardener. The resulting resin is then hardened and further treated as in a single-stage process as described above.

What is claimed is:

1. A method for manufacturing macroporous vitreous carbon comprising the steps of:
   hardening a thermosetting carbonizable resin including about 1 to about 10 weight-percent of a fatty acid salt having about 10 to about 20 carbon atoms, said salt being soluble in said resin; and
   pyrolizing the hardened resin to effect carbonization of said resin and substantially complete volatilization of said salt.

2. The method according to claim 1, wherein the resin is selected from the group consisting of furfuryl alcohol and phenol-furane resins.

3. The method according to claim 2, wherein the fatty acid salt is selected from the group consisting of magnesium and zinc salts of undecylenic, stearic and palmitic acids.

4. The method according to claim 3, wherein the resin is hardened at temperatures of about 150° to 200° C.

5. The method according to claim 3 wherein the pyrolysis is carried out at temperatures of up to about 1100° C.

6. The method according to claim 3 further comprising the step of activating the vitreous carbon.

7. The method according to claim 1, wherein the fatty acid salt is zinc stearate.

8. The method according to claim 1, wherein the fatty acid salt is zinc undecylenate.

9. The method according to claim 1 wherein p-toluenesulfonic acid is included for hardening the resin.

10. The method according to claim 1 wherein the resin is hardened at temperatures of about 150° to 200° C.

11. The method according claim 1 wherein the pyrolysis is carried out at temperatures of up to about 1100° C.

12. The method according to claim 1 further comprising the step of activating the vitreous carbon.

13. An electrochemical double-layer capacitor having at least one electrode comprising macroporous vitreous carbon prepared by hardening and pyrolysis of thermosetting carbonizable resins, characterized by the feature that about 1 to 10 weight-percent of a resin soluble salt of a fatty acid having about 10 to about 20 carbon atoms which can be volatilized without residue, is included in the resin.

14. The electrochemical double layer capacitor of claim 13 wherein said vitreous carbon is activated.

15. The electrochemical double layer capacitor of claim 13 wherein said carbonizable resin is a furfuryl alcohol resin; said fatty acid salt is selected from the group consisting of zinc and magnesium salts of stearic, palmitic, and undecylenic acids; and the resin is hardened with p-toluenesulfonic acid.

* * * * *